United States Patent
Ozturk et al.

(10) Patent No.: US 9,944,761 B2
(45) Date of Patent: Apr. 17, 2018

(54) POLY(THIENOTHIOPHENYLBORANE)S AND POLY(DITHIENOTHIOPHENYLBORANE)S FOR WHITE LIGHT EMITTING DIODES

(71) Applicant: TUBITAK (TURKIYE BILIMSEL VE TEKNOLOJIK ARASTIRMA KURUMU), Ankara (TR)

(72) Inventors: Turan Ozturk, Istanbul (TR); Emine Tekin, Kocaeli (TR); Sahin Onur, Istanbul (TR); Emine Billur Sevinis, Istanbul (TR); Mehmet Sayip Eroglu, Istanbul (TR); Ahmet Ceyhan Goren, Kocaeli (TR); Mehmet Emin Cinar, Istanbul (TR); Gulsen Turkoglu, Istanbul (TR)

(73) Assignee: TUBITAK (TURKIYE BILIMSEL VE TEKNOLOJIK ARASTIRMA KURUMU), Ankara (TR)

( * ) Notice: Subject to any disclaimer, the term of this patent is extended or adjusted under 35 U.S.C. 154(b) by 0 days.

(21) Appl. No.: 14/916,571

(22) PCT Filed: Sep. 5, 2013

(86) PCT No.: PCT/IB2013/058311
§ 371 (c)(1),
(2) Date: Mar. 4, 2016

(87) PCT Pub. No.: WO2015/033187
PCT Pub. Date: Mar. 12, 2015

(65) Prior Publication Data
US 2016/0194458 A1    Jul. 7, 2016

(51) Int. Cl.
C08G 79/08    (2006.01)
C07F 5/02    (2006.01)
(Continued)

(52) U.S. Cl.
CPC .............. C08G 79/08 (2013.01); C07F 5/027 (2013.01); C09K 11/06 (2013.01); H01L 51/008 (2013.01);
(Continued)

(58) Field of Classification Search
CPC ......... C08G 79/08; C07F 5/027; C09K 11/06; C09K 2211/1458; C09K 2211/1491; H01L 51/0036; H01L 51/0043; H01L 51/008
See application file for complete search history.

(56) References Cited

U.S. PATENT DOCUMENTS

| 4,356,429 A | 10/1982 | Tang |
| 5,399,502 A * | 3/1995 | Friend .................... C09K 11/06 438/22 |
| 2005/0001184 A1* | 1/2005 | Zanga ..................... B67C 3/281 251/63.5 |

FOREIGN PATENT DOCUMENTS

WO    WO9013148    11/1990
WO    WO2006031893 A2    3/2006
(Continued)

OTHER PUBLICATIONS

M. Mazzeo et al "Bright White Organic Light-Emitting Devices from a Single Active Molecular Material", Advanced Materials, vol. 17, No. 1, (Jan. 6, 2005), pp. 34-39.
(Continued)

*Primary Examiner* — Nicholas E Hill
(74) *Attorney, Agent, or Firm* — Gokalp Bayramoglu (57) ABSTRACT

The present invention discloses the syntheses of new polymers with defined structures, comprising dithienothiophene (DTT) and thienothiophene (TT) derivatives and boron,
(Continued)

light emitting devices of which have wide spectrum of fluorescence at visible region and potential of emitting white light.

7 Claims, 2 Drawing Sheets (51) Int. Cl.
C09K 11/06 (2006.01)
H01L 51/00 (2006.01)
H01L 51/50 (2006.01)
(52) U.S. Cl.
CPC ...... *H01L 51/0036* (2013.01); *H01L 51/0043* (2013.01); *C09K 2211/1458* (2013.01); *C09K 2211/1491* (2013.01); *H01L 51/5012* (2013.01); *Y02B 20/181* (2013.01)

(56) References Cited

FOREIGN PATENT DOCUMENTS

WO WO2007134280 A1 11/2007
WO WO2008077465 7/2008

OTHER PUBLICATIONS

Della Sala F et al "The effects of oxygen and boron functionalization on the optical properties of dithienothiophenes", Journal of Non-Crystalline Solids, North-Holland Physics Publishing. Amsterdam, NL, vol. 352 No. 23-25,(Jul. 15, 2006), pp. 2461-2464.
Turan Ozturk et al "Dithienothiophenes" Tetrahedron 61 (Jun. 25, 2005) pp. 11055-11077.
Erdal Ertas et al "A new reaction of P4S10 and Lawesson's reagent: a new method for the synthesis of dithieno[3,2-b;20,30-d]thiophenes",Tetrahedron Letters 45 (Feb. 26, 2004) pp. 3405-3407.
Ipek Osken et al "Selective syntheses of vinylenedithiathiophenes (VDTTs) and dithieno[2,3-b;20,30-d]thiophenes (DDTs); building blocks for p-conjugated systems" Tetrahedron 68 (2012) ,pp. 1216-1222.
Pinar Dundar et al "Synthesis and electrochromic properties of 3,5-diphenyl-2,6-dithiophene-2-yldithieno[3,2-b;2',3'-d]thiophene" Synthetic Metals 162 (2012) pp. 1010-1015.
Ipek Osken et al "Electrochromic behavior of poly(3,5-bis(4-bromophenyl)dithieno[3,2-b;2',3'-d]thiophene)" Thin Solid Films 519 (2011) pp. 7707-7711.
Onur Sahin et al "Investigation of electrochromic properties of poly(3,5-bis(4-methoxyphenyl)dithieno[3,2-b;2 , 3-d]thiophene)",Synthetic Metals 161 (2011) ,pp. 183-187.
Olcay Mert et al "Electrochromic properties of poly(diphenyldithieno[3,2-b;20,30-d]thiophene)",Journal of Electroanalytical Chemistry 591 (2006) ,pp. 53-58.
Asli Capan et al "Concise Syntheses, Polymers, and Properties of 3-Arylthieno[3,2-b]thiophenes",Macromolecules 45(2012)pp. 8228-8236.
Salo Gronowiitz et al "A Convenient Synthesis of Thieno[2,3-b]Thiophene",Acta Chemica Scandinavica 21(1967),pp. 812-813.

* cited by examiner

POLY(THIENOTHIOPHENYLBORANE)S AND POLY(DITHIENOTHIOPHENYLBORANE)S FOR WHITE LIGHT EMITTING DIODES

FIELD OF INVENTION

The present invention relates to thienothiophene and dithienothiophene boron polymers having specified structures, which are expected to be applied to white emitting diodes.

BACKGROUND OF THE INVENTION

Organic electronic and optoelectronic have been the focus of growing number of the researchers particularly in the fields of physics and chemistry for more than 50 years. The main attraction of this field comes from the ability to modify the chemical structure of the organic compounds in a way that the properties of the materials could directly be affected. Until the mid-1980s, their stability and performance fell short of those devices based on materials such as silicon or gallium arsenide. This situation was changed since then with the demonstration of a low voltage and efficient thin film light emitting diode, which opened the door of the possibility of using organic thin films for a new generation of electronic and optoelectronic devices. It has now proven that organic thin films are useful in a number of applications. Among them, organic light emitting device (OLED) is the most successful one, which is used now in full-color displays.

In general, two groups of organic materials, small molecules and polymers, are used in electronic and optoelectronic devices. Since polymers can be processed from solutions, they allow low cost fabrication of devices. Polymer electro-luminescent devices are described, for example, WO 2007/134280A1; US2005/01184A1; WO90/13148; US005399502; U.S. Pat. No. 4,356,429.

Understanding of their electronic structure is the key to the design of high performance optical and electronic organic devices, and some important tunings in structure or composition of an organic material can markedly alter its bulk properties. Currently, modification of the molecular structure of the conjugated materials to tune their optoelectronic properties is a challenging topic. Thiophene-based organic materials are among the most promising compounds with tuneable functional properties by proper molecular engineering. For example, thiophenes and their oligomers and polymers are not proper materials for applications in light emitting devices as they have low electron affinities and low solid-state photoluminescence efficiencies. On the other hand, converting oligothophenes into the corresponding oligothiophene-S,S-dioxides has been shown to be useful for increasing both thin film photoluminescence efficiencies and molecular energy levels.

The use of boron to alter the properties of organic electronics and optoelectronics materials has started recently and given interesting results. The reason for that is the presence of empty $p_z$ orbital of boron which behaves as strong electron withdrawing atom when it makes three bonds. It delocalizes electrons strongly when integrated to "π" systems. In organic materials chemistry, conjugated organoborane polymers are now considered as new class of organic materials with their widespread applications in electronics, optoelectronics and sensors.

In OLED technology, white light is generally obtained with multi-emissive layers to provide the three main colors, i. e. blue, green and red, combination of which gives white color. On the other hand, obtaining white color from one emissive layer is a challenge. Emission from such material needs to cover wide range of visible region.

Materials incorporating thiophene, thiophene derivatives and boron tend to emit white light (M. Mazzeo, Adv. Mater. 2005, 17, 34). Thus, it would be desirable developing materials having thiophene, thiophene derivatives and boron to obtain white light for organic light emitting diodes.

DISCLOSURE OF THE INVENTION

The invention discloses the compounds that are useful when employed as organic light emitting materials, i. e. organic light emitting diodes (OLED), to emit particularly white light. They have potential of being employed as charge transport materials in electronic devices such as organic field effect transistors (OFET), organic photovoltaic diodes and the like. The invention discloses the compounds having the formulas (I)-(X), (XI)-(XV), (XVI)-(XXVII) and (XXVIII)-(XXXVII).

(VI)

(VII)

(VIII)

(IX)

(X)

n = 1-1.000.000 inclusive

Ar = wherein
R, $R^1$, $R^2$, $R^3$ and $R^4$ are independently or equally atom chain(s)/group(s) of about 1 atom to 60 atoms. They may equally or independently have one or more of a group comprising alkyl, aryl, alkenyl, alkynyl, amine, ester, carbonate ester, carbonyl, sulphide, organosilane and thiolate.

(XI)

(XII)

(XIII)

(XIV)

(XV)

n = 1-1.000.000 inclusive wherein
R, $R^1$, $R^2$, $R^3$ and $R^4$ are independently or equally atom chain(s)/group(s) of about 1 atom to 60 atoms. They may equally or independently have one or more of a group comprising alkyl, aryl, alkenyl, alkynyl, amine, ester, carbonate ester, carbonyl, sulphide, organosilane and thiolate.

(XVI)

(XVII)

(XVIII)

(XIX)

(XX)

(XXI)

(XXII)

(XXIII)

(XXIV)

(XXV)

(XXVI)

(XXVII)

-continued wherein
R, $R^1$, $R^2$ and $R^3$ are independently or equally atom chain(s)/group(s) of about 1 atom to 60 atoms. They may equally or independently have one or more of a group comprising alkyl, aryl, alkenyl, alkynyl, amine, ester, carbonate ester, carbonyl, sulphide, organosilane and thiolate.

(XXVIII)

(XXIX)

(XXX)

(XXXI)

-continued (XXXII)

(XXXIII)

(XXXIV)

(XXXV)

(XXXVI)

(XXXVII)

-continued wherein
R, R¹, R² and R³ are independently or equally atom chain(s)/group(s) of about 1 atom to 60 atoms. They may equally or independently have one or more of a group comprising alkyl, aryl, alkenyl, alkynyl, amine, ester, carbonate ester, carbonyl, sulphide, organosilane and thiolate.

(XXXVIII)

(XXXIX)

(XL)

(XLI)

(XLII)

(XLIII)

-continued

(XLIV)

(XLV)

(XLVI)

(XLVII)

wherein
R, R¹, R², R³ and R⁴ are independently or equally atom chain(s)/group(s) of about 1 atom to 60 atoms. They may equally or independently have one or more of a group comprising alkyl, aryl, alkenyl, alkynyl, amine, ester, carbonate ester, carbonyl, sulphide, organosilane and thiolate.

Dithienothiophenes (DTT) (XXXVIII)-(XLIII) and thienothiophenes (TT) (XLIV)-(XLVII) were synthesized following the literature procedure (T. Ozturk, et al. *Tetrahedron*, 2005, 61, 11055; E. Ertas, et al. *Tetrahedron Lett.* 2004, 45, 3405; I. Osken, *Tetrahedron*, 2012, 68, 1216; P. Dundar, *Synth. Met.* 2012, 162, 1010; I. Osken, *Thin Solid Films*, 2011, 519, 7707; O. Sahin, *Synth. Met.* 2011, 161, 183; O. Mert, *J. Electroanal. Chem.* 2006, 591, 53; A. Capan, *Macromolecules* 2012, 45, 8228). Corresponding polymers (I)-(X) of DTTs and TTs were produced by lithiating bromo-DTTs (XXXVI)-(XLI) and TTs (XLII)-(XLV) with n-BuLi, which was followed by addition of aryldimethoxyborane. The DTT analogues comprising Se heteroatom(s), the DTTs having sulfurs in the rings looking at the same direction, TT analogues comprising Se atom(s) and TTs having sulfurs in the rings looking at the same direction were synthesized following the literature method (Gronowitz, S.; Persson, B. Acta Chem. Scand. 1967, 21, 812-813; WO2008/077465).

EXAMPLE

A General Procedure for the Synthesis of the Polymers; Polymer (VIII, Ar=Mesityl, $R^4$=H).

To a solution of thienothiophene (TT) (XLV, $R^4$=H) (0.2 g, 0.44 mmol) dissolved in dry THF (30 ml) under $N_2$, n-BuLi (0.8 ml, 3.3 mmol, 1.9 M) was added dropwise at −78° C., and the mixture was stirred one and half hour. The addition could be performed at any temperature between −78-+30° C. Then, the temperature was raised to room temperature and the mixture was stirred at this temperature for 20 min. Dimethoxymesityl borane (MesB(OMe)$_2$) (0.170 g, 0.88 mmol), dissolved in dry THF (5 ml) was added under nitrogen atmosphere. The reaction was stirred overnight and the solvent was removed under reduced pressure. The stirring could be between 1 min—overnight or longer, and dimethoxymesityl borane could be dissolved in any organic solvent, which does not react with dimethoxymesityl borane. The residue was dissolved in minimum amount of THF and precipitated in methanol. The precipitate was filtered and washed with methanol. Mw: 146600, Mn: 102800, Mw/Mn: 1.43, dn/dc: 0.16 mL/g (THF, 25° C.).

Example of a Device Fabrication:

Organic light emitting devices were fabricated by coating the polymers from their solution onto electrically conductive substrates. The polymer (VIII) was dissolved in a mixture of toluene/dichlorobenzene (8 mg/ml). Indium thin oxide (ITO), coated (15 ohms/sq.) on a glass, was employed as an anode electrode. PEDOT:PSS, as a hole injection layer, was spin-coated on ITO, which was dried at 110° C. for 10 min. Subsequently, polymer film, as an active layer, was coated by spin coating. Finally, LiF (1 nm) and aluminum (Al, 100 nm) was deposited under vacuum (~$10^{-6}$ mbar) by thermal evaporation technique to assemble the cathode electrodes.

Figure 1:
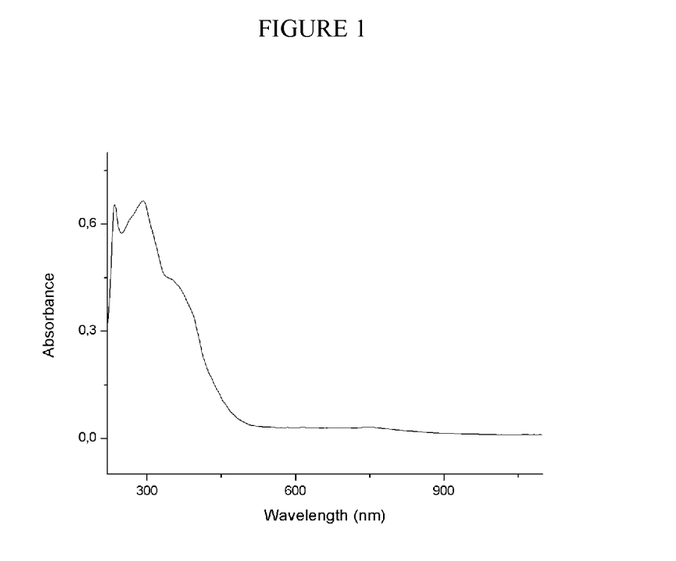
FIG. 1. UV spectrum of polymer (VIII) in THF
Figure 2:
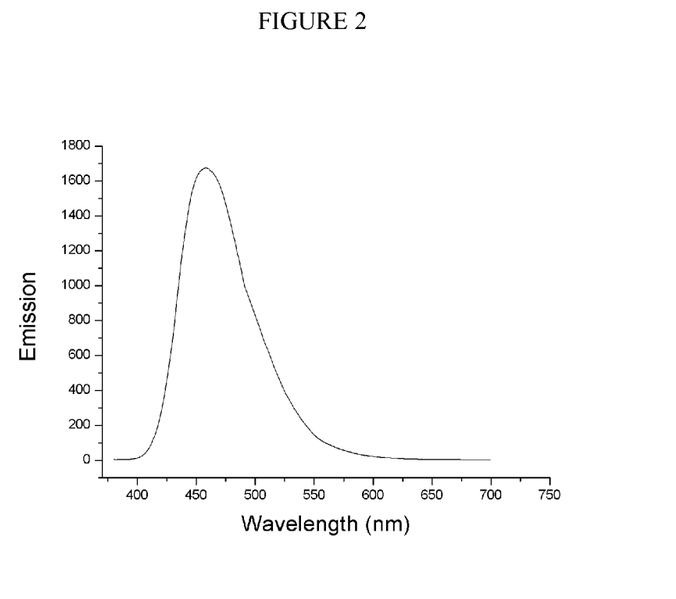
FIG. 2. Fluorescence spectrum of polymer (VIII) in THF
Figure 3:
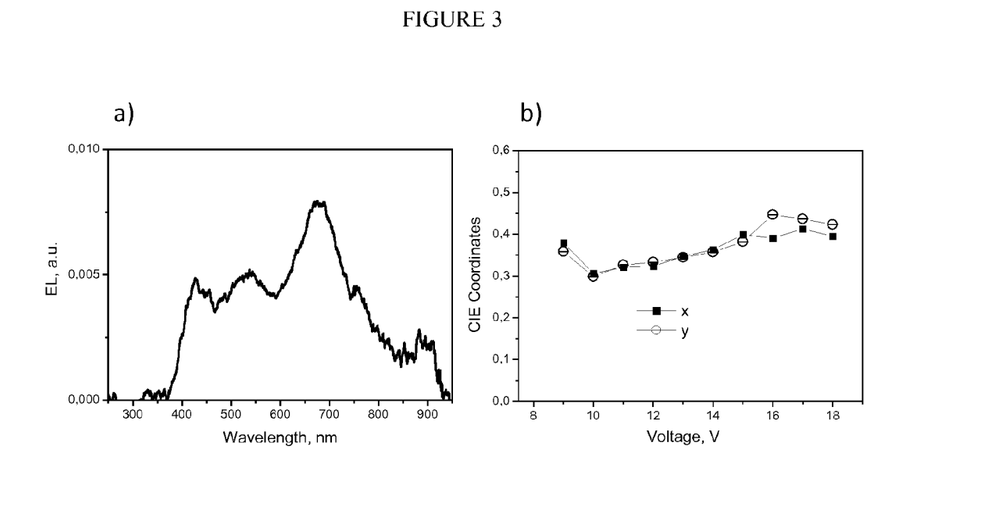
FIG. 3. a) Electroluminescent spectrum of the fabricated device of the polymer VIII (device layout: PEDOT/VIII/LiF/Al), b) CIE coordinates of the fabricated device of the polymer VIII at different voltages. The electroluminescent spectrum covers the region almost from 350 nm to 950 nm. Color coordinates are in the region for white color according to the CIE 1931 Chromaticity Diagram.
Figure 4:
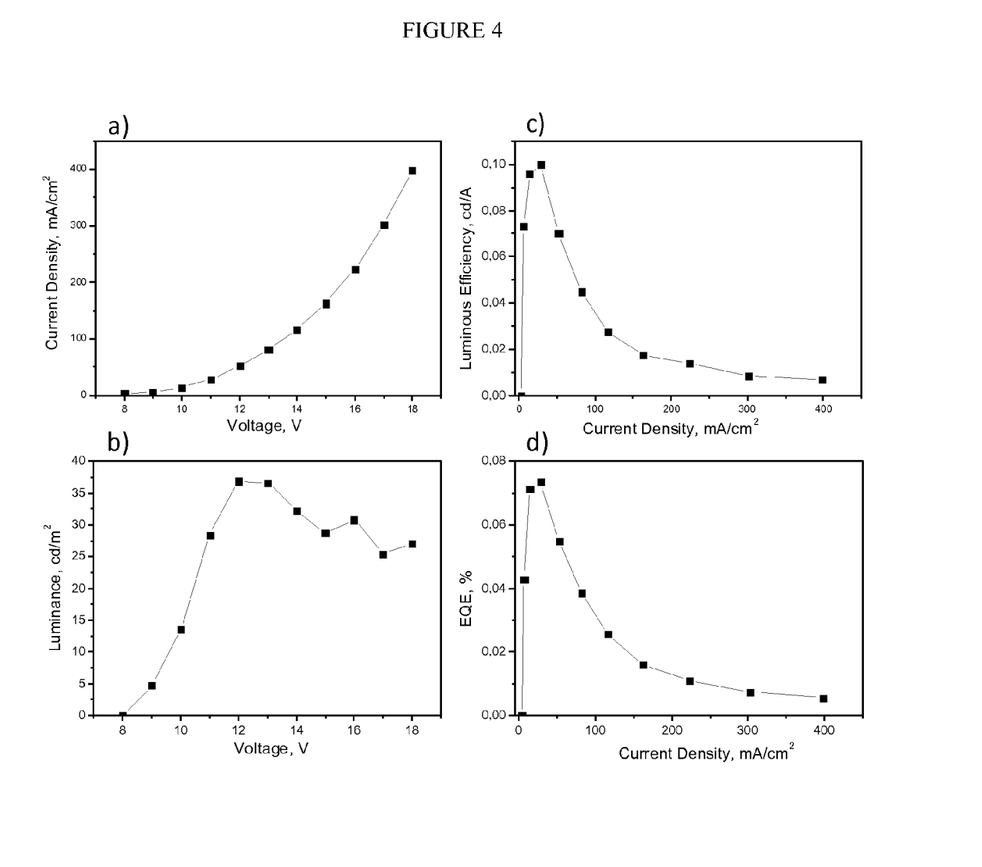
FIG. 4. OLED device characteristics: a) voltage-current b) luminance-voltage c) luminous efficiency-current density and d) external quantum efficiency-current density.

What is claimed is:

1. A polymer comprising one or more formulas selected from the group consisting of formulas (II), (III), (IV), (V), (VI), (VII), (VIII), (IX) and (X)

(II)

(III)

(IV)

(V)

(VI)

(VII)

(VIII)

-continued where, n=1-1,000,000 inclusive;
and
R, R$^1$, R$^2$, R$^3$, R$^4$, and R$^5$ are atom chain(s) of about 1 atom to 60 atoms; wherein, R, R$^1$, R$^2$, R$^3$, R$^4$, and R$^5$ may contain one or more functional group selected from the group consisting of alkyl, aryl, alkenyl, alkynyl, amine, ester, carbonate ester, carbonyl, sulphide, organosilane and thiolate.

2. A polymer comprising one or more formulas selected from the group consisting of formulas (XI), (XII), (XIII), (XIV) and (XV)

where, n=1-1,000,000 inclusive;
and

R, R¹, R², R³, R⁴, and R⁵ are atom chain(s) of about 1 atom to 60 atoms; wherein R, R¹, R², R³, R⁴, and R⁵ may contain one or more functional group selected from the group consisting of alkyl, aryl, alkenyl, alkynyl, amine, ester, carbonate ester, carbonyl, sulphide, organosilane and thiolate.

3. A polymer comprising one or more formulas selected from the group consisting of formulas (XVI), (XVII), (XVIII), (XIX), (XXII), (XXIII), (XXIV), (XXV), (XXVI) and (XXVII)

where,

-continued n=1-1,000,000 inclusive;
and

R, $R^1$, $R^2$, and $R^3$ are atom chain(s)/group(s) of about 1 atom to 60 atoms; wherein, R, $R^1$, $R^2$, and $R^3$ may contain one or more functional group selected from the group consisting of alkyl, aryl, alkenyl, alkynyl, amine, ester, carbonate ester, carbonyl, sulphide, organosilane and thiolate.

4. A polymer comprising one or more formulas selected from the group consisting of formulas (XXVIII), (XXIX), (XXX), (XXXI), (XXXII), (XXXIII), (XXXIV), (XXXV), and (XXXVII)

(XXVIII)

(XXIX)

(XXX)

-continued

(XXXI)

(XXXII)

(XXXIII)

(XXXIV)

(XXXV)

(XXXVII)

where, n=1-1,000,000 inclusive;
and
R, R¹, R², and R³ are atom chain(s)/group(s) of about 1 atom to 60 atoms; wherein, R, R¹, R², and R³ may contain one or more functional group selected from the group consisting of alkyl, aryl, alkenyl, alkynyl, amine, ester, carbonate ester, carbonyl, sulphide, organosilane and thiolate.

5. A blend comprising a polymer given in any one of claims 1 to 4.

6. A formulation comprising a polymer given in any one of claims 1 to 4.

7. A polymer comprising formula I where, n=2-1,000,000 inclusive;
and
R, and R¹ are atom chain(s) of about 1 atom to 60 atoms; wherein, R and R¹ contain one or more functional group selected from the group consisting of aryl, alkenyl, alkynyl, amine, ester, carbonate ester, carbonyl, sulphide, organosilane and thiolate.

* * * * *